(12) United States Patent
Hutchenson et al.

(10) Patent No.: US 7,153,981 B2
(45) Date of Patent: *Dec. 26, 2006

(54) SUPERCRITICAL FLUID PHASE SYNTHESIS OF METHYLENE LACTONES USING OXYNITRIDE CATALYST

(75) Inventors: Keith W. Hutchenson, Lincoln University, PA (US); Kostantinos Kourtakis, Media, PA (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/169,102

(22) Filed: Jun. 28, 2005

(65) Prior Publication Data

US 2006/0025609 A1 Feb. 2, 2006

Related U.S. Application Data

(60) Provisional application No. 60/591,504, filed on Jul. 27, 2004.

(51) Int. Cl.
C07D 307/02 (2006.01)
C07D 407/00 (2006.01)
C07D 305/12 (2006.01)
C07D 307/26 (2006.01)
C07D 307/34 (2006.01)

(52) U.S. Cl. ........................ 549/295; 549/326
(58) Field of Classification Search .......... 549/295, 549/326
See application file for complete search history.

(56) References Cited

U.S. PATENT DOCUMENTS 6,313,318 B1  11/2001  Coulson et al.

2003/0166949 A1  9/2003  Manzer et al.
2006/0025604 A1*  2/2006  Hutchenson et al. ........ 549/263
2006/0025606 A1*  2/2006  Hutchenson et al. ........ 549/263

FOREIGN PATENT DOCUMENTS

JP    10298172        * 11/1998
WO    WO9952628        10/1999
WO    WO 03/053913     7/2003

OTHER PUBLICATIONS

M. J. Climent et al., Catalysis Letter, 59 (1999) 33-38.
P. Grange et al., Applied Catalysis A: General, 114 (1994) L191-L196.
P. Grange et al., Applied Catalysis A: General, 137 (1996) 9-23.
Gang Yang et al., "On Configuration of Exchanged LA3+ On ZSM-5: A Theoretical Approach to the Improvement in Hydrothermal Stability of La-Modified ZSM-5 Zeolite" Journal of Chemical Physics (2003) 119, (18) 9765-9770.
K. W. Hutchenson, "Organic Chemical Reactions and Catalysis in Supercritical Fluid Media", Supercritical Fluid Technology in Materials Science and Engineering, Y. P. Sun (Ed), Marcel Dekker: New York (2002) p. 87-187.
Kirk-Othmer Encyclopedia of Chem. Technology, 4th Ed., vol. 23, p. 452-477.
International Search Report.

* cited by examiner

Primary Examiner—Thomas McKenzie
Assistant Examiner—Niloofar Rahmani

(57) ABSTRACT

Process for converting certain lactones to their alpha-methylene substituted forms in a supercritical or near-critical fluid phase reaction using an oxynitride catalyst or a composite oxynitride catalyst incorporating lithium, sodium, potassium, rubidium, cesium, magnesium, calcium, strontium, or barium or combinations thereof.

10 Claims, No Drawings

SUPERCRITICAL FLUID PHASE SYNTHESIS OF METHYLENE LACTONES USING OXYNITRIDE CATALYST

CROSS-REFERENCE TO RELATED APPLICATION

This application claims priority under 35 U.S.C. §119 from U.S. Provisional Application Ser. No. 60/591,504, filed Jul. 27, 2004.

FIELD OF INVENTION

The invention pertains to a method of producing unsubstituted and substituted alpha-methylene lactones from reaction of lactones with formaldehyde in a supercritical or near-critical fluid phase in the presence of an oxynitride catalyst or oxynitride catalyst composite.

BACKGROUND

Alpha-methylene-gamma-butyrolactone and methyl alpha-methylene-gamma-butyrolactone are useful monomers in the preparation of both homopolymers and copolymers. In addition, the alpha-methylene-gamma-butyrolactone group is an important structural feature of many sesquiterpenes of biological importance.

U.S. Pat. No. 6,313,318 describes a method for converting certain starting lactones to alpha-methylene substituted lactones using a so-called basic catalyst that is made by treating silica with an inorganic salt of Ba, Mg, K, Cd, Rb, Na, Li, Sr, and La. A problem with silica-based catalysts is that they are hydrothermally unstable under reaction conditions involving temperatures above about 250° C. In addition, regeneration cycles involving air produce water at high temperature, and the water can change the porosity and activity of the catalyst.

U.S. 2003-0166949 A1 describes a method for converting certain starting lactones to alpha-methylenelactones in a supercritical fluid (SCF) phase using a heterogeneous so-called basic catalyst that can be selected from the Group I, Group II, and Lanthanide Group oxides, hydroxides, carbonates, hydrogen carbonates, silicates, oxalates, carboxylates, acetates and phosphates, and mixtures thereof, any of which may be supported or unsupported. The basic catalyst may include additives and promoters to enhance catalyst efficiency. The method involves a reaction between the starting lactone and formaldehyde and may be carried out in a batch or continuous mode. The process can be run in either a single homogeneous phase over the catalyst, or the reactants and SCF may be in two different phases over the catalyst. The temperature of the reaction can range from about 70° C. to about 400° C., with a preferred range of about 100° C. to about 350° C. A more preferred range is about 200° C. to about 350° C. Pressure ranges are those required to achieve the supercritical or near-critical state under a given set of reaction conditions. The pressure of the reaction can range from about 5 to about 60 MPa, with a preferred range of about 15 to about 40 MPa.

The prior art in this area involves the use of supported catalysts on silica, which are known to be hydrothermally unstable (see for instance, WO9952628A1). Under reaction conditions, or after repeated regeneration cycles, a hydrothermally unstable material will show catalytic performance that will deteriorate with time.

Aluminum phosphorous oxynitrides are a relatively new category of materials, which may have unique properties for base catalyzed chemistry. These materials are believed to have adjustable acid/base properties. The aluminum phosphorus oxynitrides, which were first described by M. J. Climent (M. J. Climent et al., Catalysis Letter, 59 (1999) 33–38; P. Grange et al., Applied Catalysis A: General 114 (1994) L191–L196; P. L. Grange et al., Applied Catalysis A: General, 137 (1996) 9–23) have been shown to be active for various base catalyzed condensation reactions (e.g., arylsulfones with substituted benzaldehydes). Structural information is not available. However, depending on the nitridation temperature and other conditions, and therefore degree of incorporation of nitrogen into the structure of these materials, it was shown that the relative proportion of acidic and basic sites in the catalyst could be adjusted. However, the use of these materials for lactone conversion has not been described, either as the oxynitrides or as composite catalysts in which various Group I and/or Group II elements are incorporated into the oxynitrides.

Although phosphorus oxynitride materials might be expected to possess a significant advantage in hydrothermal stability compared to conventional silica catalysts, the catalytic activity of such materials for lactone conversion reactions cannot be predicted because of the unpredictable nature of catalysis in general.

It would be advantageous to have a catalyst that is hydrothermally stable at high temperatures and whose activity does not decay with time on stream (TOS) or after several high temperature oxidizing regenerations.

SUMMARY OF THE INVENTION

This invention relates to the discovery that the phosphorus oxynitrides and oxynitride composites (as defined below) are surprisingly active for lactone conversion chemistry, with the advantage that they should possess superior hydrothermal stability compared to prior art supported silica catalysts.

In its first aspect, the present invention is a process for preparing a reaction product comprising an alpha-methylene lactone of the Formula II, said process comprising combining a lactone of the Formula I with formaldehyde derived from a formaldehyde source and a solvent to produce a reaction mixture,

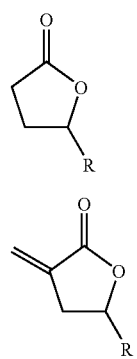

wherein R is selected from the group consisting of hydrogen, methyl, ethyl, and straight or branched $C_3$–$C_5$ alkyl; at a temperature and pressure sufficient to cause the reaction mixture to exist as a supercritical or near-critical fluid, said temperature being sufficient to cause the formation of said alpha-methylene lactone of Formula II; said reaction mixture being in the presence of a catalyst; said catalyst being an oxynitride catalyst of the nominal formula Al$_1$Si$_x$ P (O$_{(4+2x)-y}$)N$_{2/3\ y}$ wherein;

x=0 to 1, and y=0.001 to 2.

In its second aspect the invention involves the same reaction wherein the oxynitride catalyst is made by a process comprising:
(a) combining AlCl$_3$ or aluminum alkoxides containing 1–20 carbon atoms with water;
(b) adding H$_3$PO$_4$ to the product of step (a);
(c) optionally adding silicon alkoxide to the product of step (b);
(d) adding NH$_4$OH to the product of step (b), or to the product of step (c) if step (c) is performed;
(e) drying the product of step (d);
(f) optionally washing the product of step (e); and
(g) heating the product of step (e) or (f) in NH$_3$.

In its third aspect, the invention involves the same reaction wherein the catalyst is a composite catalyst that is a reaction composite of the oxynitride catalyst and certain elements selected from Group I and/or Group II of the Periodic Table, made by a process comprising:
(a) contacting (i) the oxynitride catalyst with (ii) a solution comprising a solvent and a compound of at least one element selected from the group consisting of lithium, sodium, potassium, rubidium, cesium, magnesium, calcium, strontium and barium;
(b) drying the product of step (a) to remove at least a portion of said solvent;
(c) heating the product of step (b) to a temperature in the range of 350° C. to 550° C. to produce a catalyst precursor; and
(d) flushing at a preselected flow rate an oxygen-containing gas over said catalyst precursor either during step (c), or after step (c) while the temperature is still in the range of 350° C. to 550° C. to produce the composite catalyst in which the at least one element is present in said composite catalyst in an amount from about 0.1% to about 40% by weight of the combined weight of the oxynitride catalyst and the element.

Catalysts used in the present invention might be expected to confer an advantage over silica-based catalysts in terms of hydrothermal stability based on the theory that any enhancement of the lattice energy of a solid will yield a thermally and hydrothermally stable material. In terms of their fundamental inorganic properties, phosphate systems are more ionic compared to the silicon oxides by virtue of the phosphate group relative to the oxygen anion. This will in turn strengthen the interactions between the positively and negatively charged species in the lattice, stabilizing the structure. This explanation has been applied to the incorporation of La$^{3+}$ in zeolitic structures (Yang, Gang; Wang, Yan; Zhou, Danhong; Zhuang, Jianqin; Liu, Xianchun; Han, Xiuwen; Bao, Xinhe, "On configuration of exchanged La3+ on ZSM-5: a theoretical approach to the improvement in hydrothermal stability of La-modified ZSM-5 zeolite" Journal of Chemical Physics (2003), 119(18), 9765–9770).

DETAILED DESCRIPTION OF THE INVENTION

The following terms generally are abbreviated as follows:
alpha-methylene-gamma-butyrolactone is abbreviated MBL;
gamma-butyrolactone is abbreviated GBL;
gamma-valerolactone is abbreviated GVL;
alpha-methylene-gamma-valerolactone is abbreviated MVL;
gamma-methyl alpha methylene gamma butyrolactone is abbreviated MeMBL;
gas chromatography is abbreviated GC;
mass spectroscopy is abbreviated MS;
time on stream is sometimes abbreviated TOS;
standard cubic centimeters is abbreviated sccm,
"supercritical fluid" is abbreviated SCF; and
"weight hour space velocity" is abbreviated WHSV.

The process of the present invention concerns a supercritical or near-critical fluid phase methylation of lactones of Formula I to yield alpha-methylene lactones of Formula II.

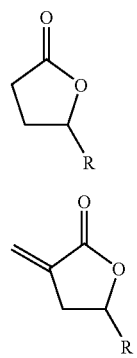

Specifically, lactone of Formula I is reacted with formaldehyde to give a reaction product comprising alpha methylene lactones of Formula II. The substituent —R group is selected from the group consisting of hydrogen, methyl, ethyl, and straight or branched C$_3$–C$_5$ alkyl. Sometimes produced is an internal isomer of the lactone of Formula II, represented by Formula III, below.

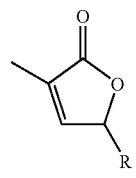

In a preferred embodiment the lactone of Formula I is gamma-butyrolactone (R is H) and the alpha-methylene lactone of Formula II is alpha-methylene-gamma-butyrolactone. In a most preferred embodiment the lactone of Formula I is gamma-valerolactone (R is CH$_3$) and the alpha-methylene lactone of Formula II is alpha-methylene-gamma-valerolactone.

The process of the present invention is conducted at reaction conditions to achieve a supercritical or near-critical fluid state. The temperature is in the range of from about 70° C. to about 400° C. A temperature in the range of from about 100° C. to about 350° C. is preferred. A temperature in the range of from about 200° C. to about 350° C. is most preferred. The pressure is in the range of from about 5 MPa to about 60 MPa, with a preferred range of from about 15 MPa to about 40 MPa. The catalyst contact time and temperature can be selected to achieve desired yields and selectivities. Contact time can be manipulated by increasing or decreasing flow rates over the catalyst.

The lactones of Formula I, formaldehyde, and the solvent can be in a homogeneous supercritical fluid phase. Alternatively the lactones of Formula I, formaldehyde, and solvent may be in two different phases (one supercritical) over the solid catalyst.

The formaldehyde may be supplied to the reaction in the form of an aqueous solution (formalin), anhydrous formaldehyde, formaldehyde hemiacetal, a low molecular weight polyformaldehyde (paraformaldehyde), or formaldehyde trimer (trioxane). The use of paraformaldehyde, trioxane, or anhydrous formaldehyde is preferred since this reduces the need to remove water from the process. Hemiacetals work effectively, but require separate steps to release the formaldehyde from the alcohol and to recover and recycle the alcohol.

The oxynitride catalyst used in the present invention is a mixed phase material that may be represented by the nominal formula:

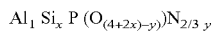

wherein x=0 to 1, and y=0.001 to 2.

The catalyst can be made by a process (is obtainable by a process) that comprises the steps of:
(a) combining $AlCl_3$ or aluminum alkoxides containing 1–20 carbon atoms with water;
(b) adding $H_3PO_4$ to the product of step (a);
(c) optionally adding silicon alkoxide to the product of step (b);
(d) adding $NH_4OH$ to the product of step (b), or to the product of step (c) if step (c) is performed;
(e) drying the product of step (d);
(f) optionally washing the product of step (e); and
(g) heating the product of step (e) or (f) in $NH_3$.

The relative number of acid and base sites on the catalyst can be adjusted by varying the time and temperature of step (g). The nitridation step in $NH_3$ introduces nitrogen into the lattice of the oxide, presumably through direct substitution of oxygen. This nitride formation (nominal $N^{3-}$) introduces basic sites on the catalyst surface.

The alkoxides of aluminum used in steps (a) or of silicon in step (c) may include any alkoxide that contains from 1 to 20 carbon atoms and preferably contains 1 to 5 carbon atoms in the alkoxide group. $C_1$–$C_4$ alkoxides such as aluminum n-butoxide and aluminum isopropoxide are suitable. Tetraethylorthosilicate is an example of a silicon alkoxide for step (c), although other alkoxides containing silicon, such as tetramethoxysiloxane can be used.

Commercially available alkoxides can be used. However, other routes can be used to prepare inorganic alkoxides. Examples include alkoxides prepared by the direct reaction of zero valent metals with alcohols in the presence of a catalyst. Many alkoxides can be formed by reaction of metal halides with alcohols. Alkoxy derivatives can be synthesized by the reaction of the alkoxide with alcohol in a ligand interchange reaction. Direct reactions of metal dialkylamides with alcohol also form alkoxide derivatives. Additional examples are disclosed in "Metal Alkoxides" by D. C. Bradley et al., Academic Press, (1978).

For step (a), aluminum chloride is preferred. For step (c), tetraethylorthosilicate is preferred.

For step (e), the drying may be done in air or an inert gas such as nitrogen, helium or argon.

In another embodiment, the oxynitride catalyst may be used to form a composite catalyst that is a reaction product of certain catalytic Group I and/or Group II elements of the Periodic Table and the oxynitride catalyst. Such catalysts can be made by (are obtainable by) a process that comprises the steps of:
(a) contacting (i) the oxynitride catalyst with (ii) a solution comprising a solvent and a compound of at least one element selected from group consisting of lithium, sodium, potassium, rubidium, cesium, magnesium, calcium, strontium and barium;
(b) drying the product of step (a) to remove at least a portion of said solvent;
(c) heating the product of step (b) to a temperature in the range of 350° C. to 550° C. to produce a catalyst precursor; and
(d) flushing at a preselected flow rate an oxygen-containing gas over said catalyst precursor either during step (c), or after step (c) while the temperature is still in the range of 350° C. to 550° C. to produce the composite catalyst, in which the at least one element is present in said composite catalyst in an amount from about 0.1% to about 40% by weight of the combined weight of the oxynitride catalyst and the element.

The inclusion of an appropriate Group I and/or Group II element into the oxynitride catalyst may cause a shift in the relative number of acid and base sites.

Organic compounds such as the carboxylates, such as acetate, propionate, butyrate, and 2-ethylhexanoate of a catalytic element selected from the group consisting of lithium, sodium, potassium, rubidium, cesium, magnesium, calcium, strontium and barium are dissolved in aqueous or non-aqueous solvent and contacted with the oxynitride catalyst. Organic compounds containing acetates are preferred. Other organic anions such as acetylacetonates can be used. The amount of organic compound should be chosen to provide to the final composite catalyst from 0.1 wt % to 40 wt % of the element relative to the combined weight of the oxynitride catalyst plus the element (as opposed to the compound of which the element is a part). The resulting material is allowed to dry, preferably in a nitrogen environment for an extended time. The purpose of the drying is to remove at least a portion of the solvent in which the organic compound is dissolved.

Organic compounds such as the alkoxides can also be used. Organic alkoxides of an element selected from the group consisting of lithium, sodium, potassium, rubidium, cesium, magnesium, calcium, strontium, and barium can contain from one to 20 carbon atoms and preferably 1 to 5 carbon atoms in the alkoxide group. The organic alkoxide should be soluble in the solvent. Most alkoxides can be dissolved in non-aqueous solutions such as ethanol, propanol, or isopropyl alcohol. Subsequent methods for introducing the element and drying are the same.

The dried material is then heated (for example in an alumina boat placed in a tube furnace) at an ambient temperature of 350° C. to 550° C. (The temperature of the catalyst material may be somewhat higher because of exothermic reactions taking place on the material.) A temperature between 450° C. and 550° C. is preferred. Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/min was found to be acceptable. Use of sufficiently high airflow rates are preferred to produce a high surface area material. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 350° C. to 550° C. For acetate precursors, 450° C. to 550° C. is required. Heating times can range from 30 minutes to 48 hours. The final heating step preferably is performed in air for at least 30 minutes.

In some cases, reaction conditions may result in a decrease of catalyst efficiency. In these situations it may be useful to periodically reactivate the catalyst. For example, contacting the present catalysts, when activity drops below an acceptable level, with oxygen at elevated temperatures may have the effect of reactivating the catalyst. Contact temperatures with oxygen may range from about 225° C. to about 500° C., with temperatures of about 250° C. to about 425° C. being preferred.

Thermal and hydrothermal stability are required for the catalyst to withstand one or repeated regeneration cycles without permanently degrading catalyst performance.

The present method exploits several advantages of using a supercritical fluid (SCF) as the reaction solvent. SCFs are attractive media for conducting chemical transformations, primarily because the solvent and transport properties of a single solution, including the density, can be varied appreciably and continuously with relatively minor changes in temperature or pressure. The density variation in a SCF also influences the chemical potential of solutes and thus reaction rates and equilibrium constants. Thus, the solvent environment can be optimized for a specific reaction application by tuning the various density-dependent fluid properties. For a discussion of advantages and applications of supercritical fluid media for chemistry and catalysis, see Hutchenson, K. W., "Organic Chemical Reactions and Catalysis in Supercritical Fluid Media," in *Supercritical Fluid Technology in Materials Science and Engineering*, Y.-P. Sun (ed.), Marcel Dekker: New York (2002), pp. 87–187.

A fluid is in the SCF state when the system temperature and pressure exceed the corresponding critical point values defined by the critical temperature ($T_c$) and pressure ($P_c$) For pure substances, the critical temperature and pressure are the highest at which vapor and liquid phases can coexist. Above the critical temperature, a liquid does not form for a pure substance, regardless of the applied pressure. Similarly, the critical pressure and critical molar volume are defined at this critical temperature corresponding to the state at which the vapor and liquid phases merge. Similarly, although more complex for multicomponent mixtures, the mixture critical state is identified as the condition at which the properties of coexisting vapor and liquid phases become indistinguishable. For a discussion of supercritical fluids, see *Kirk-Othmer Encycl. of Chem. Technology*, 4$^{th}$ Ed., Vol. 23, pg. 452–477.

In addition to typical factors such as chemical inertness, cost, toxicity, etc., the critical temperature must be considered when selecting a potential solvent for conducting chemical transformations in the SCF regime. For practical applications, thermal and catalytic chemical reactions can only be conducted in a relatively narrow temperature range. Lower temperatures result in unacceptable reaction rates, and higher temperatures can result in significant selectivity and yield losses as well as catalyst deactivation. To obtain practical solvent densities and the corresponding density-dependent properties, this temperature optimization must be balanced against a general desire to operate in the vicinity of the mixture critical point of the reaction system to fully exploit the potential advantages afforded by SCF operation. The phase behavior of the reaction mixture, which is strongly influenced by the solvent critical temperature, is fundamentally important in defining this operating window, so one must select a solvent to provide the desired phase behavior. The phase behavior of SCF systems can also be manipulated to control the number and composition of coexisting phases, thus controlling both reaction effects as well as the separation of products or homogeneous catalysts from the reaction mixture.

In practice, a number of desirable properties characteristic of the SCF state are also realized in the expanded liquid region that exists at temperatures and pressures slightly below this critical point. Hence, for the purposes of this invention, the term "supercritical fluid" also includes such "near-critical fluids," where the fluid is either at or below the critical temperature and the properties begin to approach those of a supercritical fluid. For the purposes of this invention, a "near-critical fluid" is considered to exist at those conditions where the fluid is at temperatures from about 75% of the critical temperature to about 100% of the critical temperature, and at pressures from about 25% of the critical pressure to about 100% of the critical pressure.

One can visually observe the phase behavior of the reaction mixture by conducting the reaction in a vessel equipped with a transparent window, or by simulating the reaction mixture with a solution of similar concentration in such a vessel. Systematic determination of the phase boundaries of the reaction mixture can be determined by standard techniques using such a vessel that is also equipped with a means of varying the vessel volume at fixed composition and temperature. The vessel is loaded with the various components at the specified composition of the reaction mixture, heated to the reaction temperature, then the solution pressure is varied by changing the vessel volume until a phase transition is visually observed. After measuring the phase boundary of a solution of interest over the range of anticipated compositions, one can define the operating conditions necessary to achieve the supercritical or near-critical state for conducting the desired reaction.

Any suitable SCF solvent may be used in the process of this invention, including, but not limited to, carbon dioxide, nitrous oxide, sulfur hexafluoride, fluoromethane, trifluoromethane, tetrafluromethane, ethane, ethylene, propane, propanol, isopropanol, propylene, butane, butanol, isobutane, isobutene, pentane, hexane, cyclohexane, benzene, toluene, o-xylene, water, and mixtures thereof, provided that it is inert to all reagents and products. Preferred SCF solvents include carbon dioxide or a C1–C6 alkane, optionally substituted with Cl, F or Br. More preferred supercritical fluids are carbon dioxide, trifluoromethane, pentane, and propane.

Separation and/or purification of the desired products, including MBL or MeMBL, from unreacted starting lactone and/or reaction byproducts may be performed by processes known in the art. A particularly suitable method to recover the desired product is to polymerize MBL in GBL solution, or MeMBL in GVL solution, using standard free-radical polymerization, isolate the polymer by precipitation, and then thermally depolymerize back to MBL or MeMBL, as the case may be, by heating under vacuum. Finally, MBL can be separated from GBL by melt crystallization. Another effective method is liquid-liquid extraction.

Non-limiting reactors suitable for the process of the instant invention include tubular, fluidized bed, fixed bed, trickle bed, transport bed and stirred tank reactors. The process can be run in either batch or continuous mode as described, for example, in H. Scott Fogler, *Elements of Chemical Reaction Engineering*, $2^{nd}$ Edition, Prentice-Hall Inc, CA, 1992. The process can also be run in either a single homogeneous phase over the solid catalyst, or the reactants and SCF may be in two different phases over the solid catalyst.

Selectivities and yields of product may be influenced by the total contact time with the catalyst. As stated previously, yields and selectivities may be increased by adjusting flow rates.

Catalyst Used in the Example of this Invention $Al_1 Si_x P (O_{(4+2x)-y})N_{2/3\ y}$, x=0, y is Approximately 0.39 (Prepared Using 800° C. Nitridation Conditions, 16 Hours)

115.88 g (0.86 moles) of aluminum trichloride (Alfa Aesar, 8848) was hydrolyzed with 322 g of water and left in solution overnight. One half of this hydrolyzed solution was used. 28.6 ml of 86% $H_3PO_4$ (JT Baker) was stirred into this half of the solution and was stirred well. After adding 116 ml of ammonium hydroxide (20–30%, EM Science), the material turned into a thick gel. After aging overnight, the material was dispersed with 300 ml of isopropyl alcohol (EM Sciences, Omnisolve) filtered and washed with two 100 ml portions of isopropyl alcohol.

The material was nitrided by placing the material in a tube furnace and heated in anhydrous ammonia. 7.486 g of the solid described above was loaded in an alumina boat, which was placed into a tube furnace and purged in $N_2$ for 40 minutes (100 sccm $N_2$). The sample was heated to 70° C. in nitrogen and allowed to soak for 1 hour and then to 500° C. in $N_2$ for 4 hours. The $N_2$ was replaced with 100 sccm anhydrous $NH_3$, and the powder was heated to 800° C., and allowed to soak at that temperature (in $NH_3$) for 8 hours. After replacing the $NH_3$ with 100 sccm $N_2$, the sample was cooled to 500° C. and held at that temperature for 12 hours. The cycle was repeated: the $N_2$ was replaced with 100 sccm $NH_3$, and the powder was heated to 800° C. under $NH_3$ for 8 hours, for a total heating time in $NH_3$ of 16 hours at 800° C. After switching the gas stream to 200 sccm $N_2$, the sample was allowed to slowly cool to room temperature.

In a duplicate preparation, the final product was analyzed for nitrogen content by Micro-Analysis Inc., Wilmington Del. In this analysis, a Perkin Elmer 2400 CHN analyzer was used, which uses a combustion method to convert the sample elements to simple gases ($CO_2$, $H_2O$, and $N_2$). The sample was first oxidized in a pure oxygen environment; the resulting gases were then controlled to exact conditions of pressure, temperature and volume. Finally, the product gases were separated under steady-state conditions and were measured as a function of thermal conductivity. Using this analysis, the final material contained 2.94 wt % nitrogen.

EXAMPLE

The reaction was conducted in a continuous fixed bed reactor consisting of a 0.25-inch o.d.×0.049-inch wall×4.5-inch long 316 stainless steel tube packed with 0.6772 g of the catalyst. The reactor was heated by cartridge-type electrical heaters mounted in an aluminum block enclosing the reactor. The lactone was combined with ethanol hemiacetal as the formaldehyde precursor and metered to the reactor as a liquid feed with a syringe pump. The ethanol hemiacetal was prepared by refluxing a 50 mol % paraformaldehyde solution in ethanol for four hours at 95° C., followed by cooling to room temperature and filtration. The carbon dioxide solvent was metered as a condensed liquid with a second positive-displacement pump, and the two streams were combined and heated prior to entering the reactor. This solution formed a supercritical fluid phase at the reaction conditions. Liquid-phase reactor effluent samples were collected downstream in an ice bath after venting the carbon dioxide, and reaction products were quantified by gas chromatography using diphenyl ether as an internal standard. The reactor pressure was controlled by a backpressure regulator located downstream of the reactor.

The reactant feed solution consisted of 52.3 wt % GVL with the balance made up with the ethanol hemiacetal solution. This solution resulted in a 1.2:1 ratio of formaldehyde to GVL in the reactor feed, which was metered at a rate resulting in a weight hour space velocity (WHSV) in the reactor of 1.17 g GVL/(g catalyst-h). The carbon dioxide flow rate was metered independently to give a final total organic concentration of 4.2 mol % in the reactor feed. The reactor was operated at a temperature of 300° C. and a pressure of about 23.5 MPa. The corresponding reaction profile showing conversion of GVL to MeMBL is summarized below:

| Run Time (h) | GVL Conversion (%) | MeMBL Selectivity (%) |
| --- | --- | --- |
| 1.83 | 2.4 | 56.7 |
| 3.08 | 3.8 | 39.2 |
| 4.08 | 3.4 | 37.3 |
| 5.10 | 3.1 | 35.7 |

The data show that reactions done in accordance with the process of the present invention yield the desired products with adequate conversion and high selectivity.

What is claimed is:

1. A process for preparing a reaction product comprising an alpha-methylene lactone of the Formula II, said process comprising combining a lactone of the Formula I with formaldehyde derived from a formaldehyde source and a solvent to produce a reaction mixture,

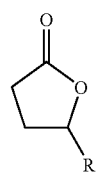

I

-continued

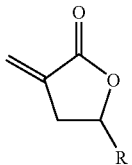

wherein R is selected from the group consisting of hydrogen, methyl, ethyl, and straight or branched $C_3$–$C_5$ alkyl;

at a temperature and pressure sufficient to cause the reaction mixture to exist as a supercritical or near-critical fluid, said temperature being sufficient to cause the formation of said alpha-methylene lactone of Formula II; said reaction mixture being in the presence of a catalyst; said catalyst being an oxynitride catalyst of the nominal formula $Al_1\ Si_x\ P\ (O_{(4+2x)-y})N_{2/3\ y}$, wherein;

X=0 to 1, and

Y=0.001 to 2.

2. The process of claim 1 wherein the catalyst is made by a process that comprises the steps of:
(a) combining $AlCl_3$ or aluminum alkoxides containing 1–20 carbon atoms with water;
(b) adding $H_3PO_4$ to the product of step (a);
(c) optionally adding silicon alkoxide to the product of step (b);
(d) adding $NH_4OH$ to the product of step (b), or to the product of step (c) if step (c) is performed;
(e) drying the product of step (d);
(f) optionally washing the product of step (e); and
(g) heating the product of step (e) or (f) in $NH_3$.

3. A process for preparing a reaction product comprising an alpha-methylene lactone of the Formula II, said process comprising combining a lactone of the Formula I with formaldehyde derived from a formaldehyde source and a solvent to produce a reaction mixture,

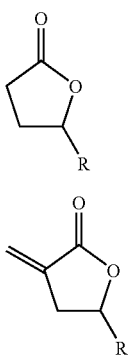

wherein R is selected from the group consisting of hydrogen, methyl, ethyl, and straight or branched $C_3$–$C_5$ alkyl;

at a temperature and pressure sufficient to cause the reaction mixture to exist as a supercritical or near-critical fluid, said temperature being sufficient to cause the formation of said alpha-methylene lactone of Formula II; said reaction mixture being in the presence of a catalyst, wherein the catalyst is a composite catalyst made by a process that comprises:

(a) contacting (i) an oxynitride catalyst of the nominal formula $Al_1\ Si_x\ P\ (O_{(4+2x)-y})N_{2/3\ y}$, wherein, X=0 to 1, and Y=0.001 to 2, with (ii) a solution comprising a solvent and a compound of at least one element selected from the group consisting of lithium, sodium, potassium, rubidium, cesium, magnesium, calcium, strontium and barium;

(b) drying the product of step (a) to remove at least a portion of said solvent;

(c) heating the product of step (b) to a temperature in the range of 350° C. to 550° C. to produce a catalyst precursor; and (d) flushing at a preselected flow rate an oxygen-containing gas over said catalyst precursor either during step (c), or after step (c) while the temperature is still in the range of 350° C. to 550° C. to produce the composite catalyst in which the at least one element is present in said composite catalyst in an amount from about 0.1% to about 40% by weight of the combined weight of the oxynitride catalyst and the element.

4. The process of claim 1 wherein R is hydrogen or methyl.

5. The process of claim 1 wherein the solvent is carbon dioxide or a $C_1$–$C_6$ alkane, optionally substituted with CL, F, or Br.

6. The process of claim 5 wherein the solvent is carbon dioxide, pentane, triflurormethane, or propane.

7. The process according to claim 1 wherein the formaldehyde is derived from a formaldehyde source selected from the group consisting of trioxane, anhydrous formaldehyde, formalin, formaldehyde oligomer, formaldehyde cyclic oligomer, formaldehyde acetal, formaldehyde hemiacetal, and formaldehyde polymer.

8. The process according to claim 7 wherein the formaldehyde source is formalin, trioxane, formaldehyde hemiacetal or paraformaldehyde.

9. The process of claim 1 further comprising separating said alpha methylene lactone from said reaction product.

10. The process of claim 1 wherein the temperature is in the range of from about 70° C. to about 400° C. and the pressure is in the range of from about 5 MPa to about 60 MPa.

* * * * *